United States Patent [19]

Naf et al.

[11] 4,011,269
[45] Mar. 8, 1977

[54] PROCESS FOR THE PREPARATION OF SESQUITERPENIC DERIVATIVES

[75] Inventors: Ferdinand Näf, Geneva; Gunther Ohloff, Bernex, both of Switzerland

[73] Assignee: Firemenich S.A., Geneva, Switzerland

[22] Filed: Aug. 20, 1975

[21] Appl. No.: 606,054

[30] Foreign Application Priority Data

Aug. 23, 1974 Switzerland .................... 11503/74

[52] U.S. Cl. ...................... 260/617 R; 260/586 R; 260/586 P; 260/617 C; 260/617 F; 260/631.5; 260/642 R
[51] Int. Cl.² ......................................... C07C 29/00
[58] Field of Search ....... 260/586 G, 586 C, 617 R, 260/617 F

[56] References Cited

UNITED STATES PATENTS

| 3,836,584 | 9/1974 | Frater et al. | 260/586 G |
| 3,879,466 | 4/1975 | Light | 260/617 F |
| 3,907,908 | 9/1975 | Light et al. | 260/586 C |
| 3,923,899 | 12/1975 | Frater et al. | 260/586 C |
| 3,925,486 | 12/1975 | Greuter et al. | 260/617 F |

*Primary Examiner*—Norman Morgenstern
*Attorney, Agent, or Firm*—Pennie & Edmonds

[57] ABSTRACT

Process for the preparation of tricyclic sesquiterpenes which comprises reacting a cyclohexadienic carbinol with a strongly basic agent. The products obtained in accordance with the process of the invention are useful ingredients in the perfumery. Some of the said products are new.

9 Claims, No Drawings

PROCESS FOR THE PREPARATION OF SESQUITERPENIC DERIVATIVES

BACKGROUND OF THE INVENTION

Patchouli oil, usually obtained by steam distillation of the dried leaves of Pogostenum Patchouli Pellet, a small plant of the family of labiates, is a very important perfume material. Owing to its property of easily and harmoniously blending with a great variety of different perfuming coingredients, Patchouli oil is used extensively in a wide range of fragrance compositions.

As a consequence, it is not astonishing to observe an ever increasing interest in the study of its composition, precisely in view of achieving its faithful reconstitution. Several cyclic sesquiterpenes have been identified among the constituents isolated sofar from pathouli oil. These derivatives include 4,8,11,11-tetramethyltricyclo [5.3.1.0$^{3,8}$] undecan-7-ol, better known under the name of patchoulol, which compound, as main constituent, plays a major role in the oil reconstitution. Patchoulol, which was first isolated already in 1869 by H. Galin [vide: C. Rend.Aca. Sci., 63, 406 (1869)] can be synthetized according to several known methods. These include those namely described by G. Buchi et al. [J. Am Chem. Soc., 83, 927 (1961); idem, 86, 4438 (1964)], S. Denishetski and D. Dumas [Chem. Comm., 1968 1287] and M. Mirrington and K. J. Schmalzl [J. Org. Chem. 37, 2871 (1972)]. These preparations possess an undeniable academic interest, however they suffer from serious disadvantages whenever it is desired to apply them to large scale industrial preparations, as the required starting materials are not commercially available and their preparation requires lengthy multistep synthetic processes.

THE INVENTION

We have now discovered that the preparation of patchoulol, as well as that of several of its derivatives and homologues, could be easily achieved by a particularly advantageous industrial process, which process comprises preparing a compound of formula (I)

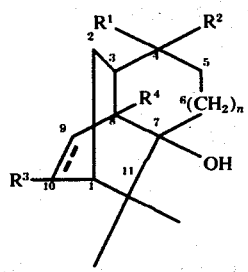

having a double or a single bound in the position indicated by the dotted line, and wherein:
each of symbols R$^1$, R$^2$, R$^3$ and R$^4$, identical or different, represents a hydrogen atom or an alkyl radical containing from 1 to 6 carbon atoms, and index n stands for zero or 1
by reacting a hydroxyl compound of formula (II)

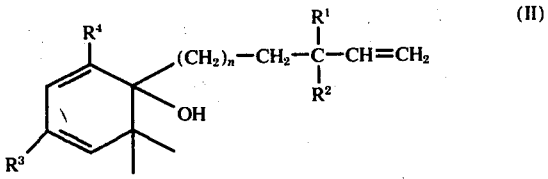

(wherein index n and symbols R$^1$, R$^2$, R$^3$ and R$^4$ have the aforementioned meaning)
with a strongly basic agent, to yield the compound of formula (I) having a double bound in the position indicated by the dotted line, and, if desired,
catalytically hydrogenating the thus obtained unsaturated product, to yield the compound of formula (I) having a single bond in the position indicated by the dotted line.

PREFERRED EMBODIMENTS OF THE INVENTION

According to a preferred embodiment of the invention, suitable basic agents include strong mineral or organic bases, preferably alkali metal hydroxides or alkoxides, such as e.g. lithium, sodium or potassium methoxide, ethoxide, butoxide or ter-butoxide. The best yields of the final products were achieved by using a base having a sterically hindered reactive centre. Thus, the preferred base is potassium or sodium ter-butoxide. An alkali metal amide, e.g. lithium diisopropylamide, can also be used satisfactorily.

The proportions in which the aforementioned bases can be used in accordance with the invention can vary within a wide range. For practical and economical reasons however, the said bases are employed at low concentrations, e.g. at from 1 to 10% by weight based on the products to be cyclised. Through these values are not deemed to be construced too restrictively, it has to be noted that at concentrations far beyond the above given upper limit, a formation of by-products of various and indefinite nature was observed, thus lowering the yields of the final desired products.

The cyclization reaction, which characterises the process of the invention, can be carried out at temperatures varying within wide limits. Their values depend primarily on the reaction time chosen, the reactants under consideration and, of course, of the pressure employed. At low pressure in fact, comprised between about 1 and 20 atm. for example, the reaction temperatures are of from about 200° to 400° C, preferably between about 230° and 320° C; whereas, at higher pressure the temperature can be lowered well beyond the lower above given value [vide: J. Am. Chem. Soc., 96, 3664 (1974)].

The reaction times also depend on a variety of factors, namely they depend on the chosen temperatures and on the volumes of the reactants to be treated. We have observed for instance that whenever the cyclization was effected in a sealed tube at about 280° C, 24 h were sufficient to achieve the complete conversion of 2,2,6-trimethyl-1-[3-methyl-pent-4-en-1-yl] cyclohexa-3,5-dien-1-ol into its corresponding tricyclic derivative, 4,8,11,11-tetramethyltricyclo [5.3.1.0$^{3,8}$] undec-9-en-7-ol.

The reaction which characterizes the process of the invention is preferably performed in an inert organic solvent. Suitable organic solvents include aliphatic, cycloaliphatic and aromatic hydrocarbons, e.g. cyclohexane, decaline, benzene and toluene.

The compounds of formula (I) having a double bound in the position indicated by the dotted line, can easily be converted into their corresponding saturated derivatives by means of a catalytic hydrogenation according to the usual techniques, for instance in the presence of a metal catalyst, preferably deposited on an inert solid support support [vide: H. O. House, "Modern Synthetic Reactions", W. A. Benjamin Inc., New York. (1972), 2$^{nd}$ edition, p. 1 and ff. ].

The hydroxyl compounds of formula (II), used as starting materials in the process of the invention, are readily accessible compounds which can be prepared by an addition of an organometallic derivative or a cyclohexadienic ketone according to the following reaction scheme:

derivative by reacting it with lithium or magnesium metal.

For example, 3-methyl-pent-4-en-1-yl-lithium could be prepared from but-2-en-1-yl bromide according to the following reaction scheme:

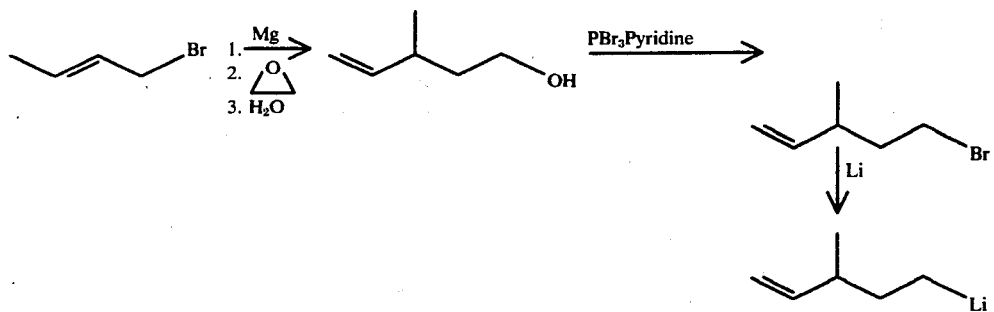

Among the compounds of formula (I), prepared in accordance with the process of the present invention, the following are of particular interest:
4,8,11,11-tetramethyltricyclo[5.3.1.0$^{3,8}$]undecan-7-ol,
4,8,11,11-tetramethyltricyclo[5.3.1.0$^{3,8}$]undec-9-en-7-ol,
8,11,11-trimethyltricyclo[5.3.1.0$^{3,8}$]undecan-7-ol,
4,11,11-trimethyltricyclo[5.3.1.0$^{3,8}$]-undec-9-en-7-ol,
4,11,11-trimethyltricyclo[5.3.1.0$^{3,8}$]undecan-7-ol,
10,11,11-trimethyltricyclo[5.3.1.0$^{3,8}$]undecan-7-ol,
10,11,11-trimethyltricyclo[5.3.1.0$^{3,8}$]undec-9-en-7-ol,

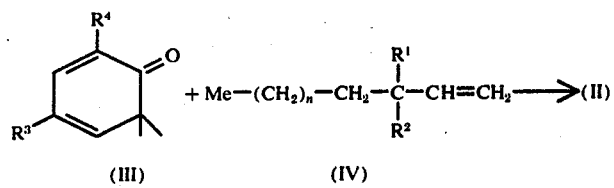

(wherein Me represents a univalent metallic function, such as MgX, in which X is a halogen atom, or Li). As organometallic derivative, a lithium derivative is preferred. The compounds of formula (III) are readily synthetized in accordance with known methods or by analogy with prior published processes [see for instance: Organic Synthesis, 46, 115 (1966)]. The hereinbelow scheme illustrates one of the said processes:

11,11-dimethyltricyclo[5.3.1.0$^{3,8}$]undecan-7-ol,
11,11-dimethyltricyclo[5.3.1.0$^{3,8}$]undec-9-en-7-ol,
7,10,10-trimethyltricyclo[4.3.1.0$^{3,7}$]dec-8-en-6-ol,
7,10,10-trimethyltricyclo[4.3.1.0$^{3,7}$]decan-6-ol.

Some of the above given compounds are new, others, like 4,8,11,11-tetramethyltricyclo[5.3.1.0$^{3,8}$]undec-9-en-7-ol, have been described in the literature [see Büchi et al., J. Am. Chem. Sec., 83, 927 (1961)], how-

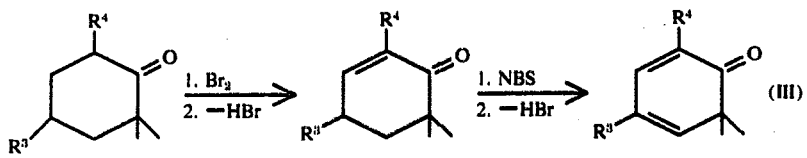

(wherein R$^3$ and R$^4$ have the abovegiven meaning and NBS stands for N-bromosuccinimide).

The compounds of formula (IV) can be obtained from an alkenyl halide by means of a Grignard type reaction with ethylene oxide [vide e.g. : Tetrahedron Letters, 1965, 4153 and Bull. Soc. Chim. France, 1963, 1385]. The alcohol thus obtained can be converted into its corresponding halide by means, e.g., of phosphorus tribromide and the halide formed converted into the desired organo-lithium or organo-magnesium ever, their organoleptie properties have never been recognized before.

The present invention has also as an object to provide a perfume composition which comprises having added as an active ingredient at least one of the compounds selected from the group consisting of:
4,8,11,11-tetramethyltricyclo[5.3.1.0$^{3,8}$]undecan-7-ol,
4,8,11,11-tetramethyltricyclo[5.3.1.0$^{3,8}$]undec-9-en-7-ol,
8,11,11-trimethyltricyclo[5.3.1.0$^{3,8}$]undecan-7-ol, 4,11,11-trimethyltricyclo 5.3.1.0$^{3,8}$]undec-9-en-7-ol,
4,11,11-trimethyltricyclo[5.3.1.0$^{3,8}$]undecan-7-ol,
10,11,11-trimethyltricyclo[5.3.1.0$^{3,8}$]undecan-7-ol,
10,11,11-trimethyltricyclo[5.3.1.0$^{3,8}$]undec-9-en-7-ol,
11,11-dimethyltricyclo[5.3.1.0$^{3,8}$]undecan-7-ol,
11,11-dimethyltricyclo[5.3.1.0$^{3,8}$]undec-9-en-7-ol,
7,10,10-trimethyltricyclo[4.3.1.0$^{3,7}$]dec-8-en-6-ol,
7,10,10-trimethyltricyclo[4.3.1.0$^{3,7}$]decan-6-ol.

The above mentioned compounds develop odoriferous notes the character of which is reminiscent of that of patchouli oil. Namely, 4,8,11,11-tetramethyltricyclo[5.3.1.0$^{3,8}$]undec-9-en-7-ol is a particularly useful compound. Its olfactive note of woodyearthy type is distinct, elegant, harmonious and extremely powerful.

The proportions in which the said compounds can be used to achieve interesting odoriferous affects in accordance with the invention can vary within wide limits. Typically, these proportions are comprised in between about 1 and 20% by weight based on the total weight of the composition to which they are added.

These proportions however are not absolute and depending on the particular odoriferous effect it is desired to achieve, they may be as small as 0.1 to 0.5% by weight of the products in which they are incorporated, namely in the case of the perfuming of soaps, cosmetics and detergents.

The said compounds can be used on their own or, more frequently, in admixture with other perfuming ingredients.

Owing to the presence of different substituents namely in position 4 and 10 of the tricyclic sesquiterpenic skeleton, the compounds of formula (I), obtained in accordance with the process of the invention, may occur in different isomeric forms. In the present specification, formula (I) is deemed to define indifferently the compounds wherein, for example, the methyl group in position 4 and the hydroxyl group in position 7 are cis or trans one relative to the other. Moreover, the presence of several centres of asymmetry in positions 1,3,4,7 and 8 implies that the compounds of formula (I) may occur in a form of one enantiomer or in a racemic form.

The following reaction scheme shows, as an example, the preparation of two enantiomers of 3-methyl-pent-4-en-1-yl bromide. - This halide can be employed for the preparation of the optically active compounds of formula (II), these latter being then used as starting materials, in accordance with the process of the invention, for the preparation of optically active end-products of formula (I).

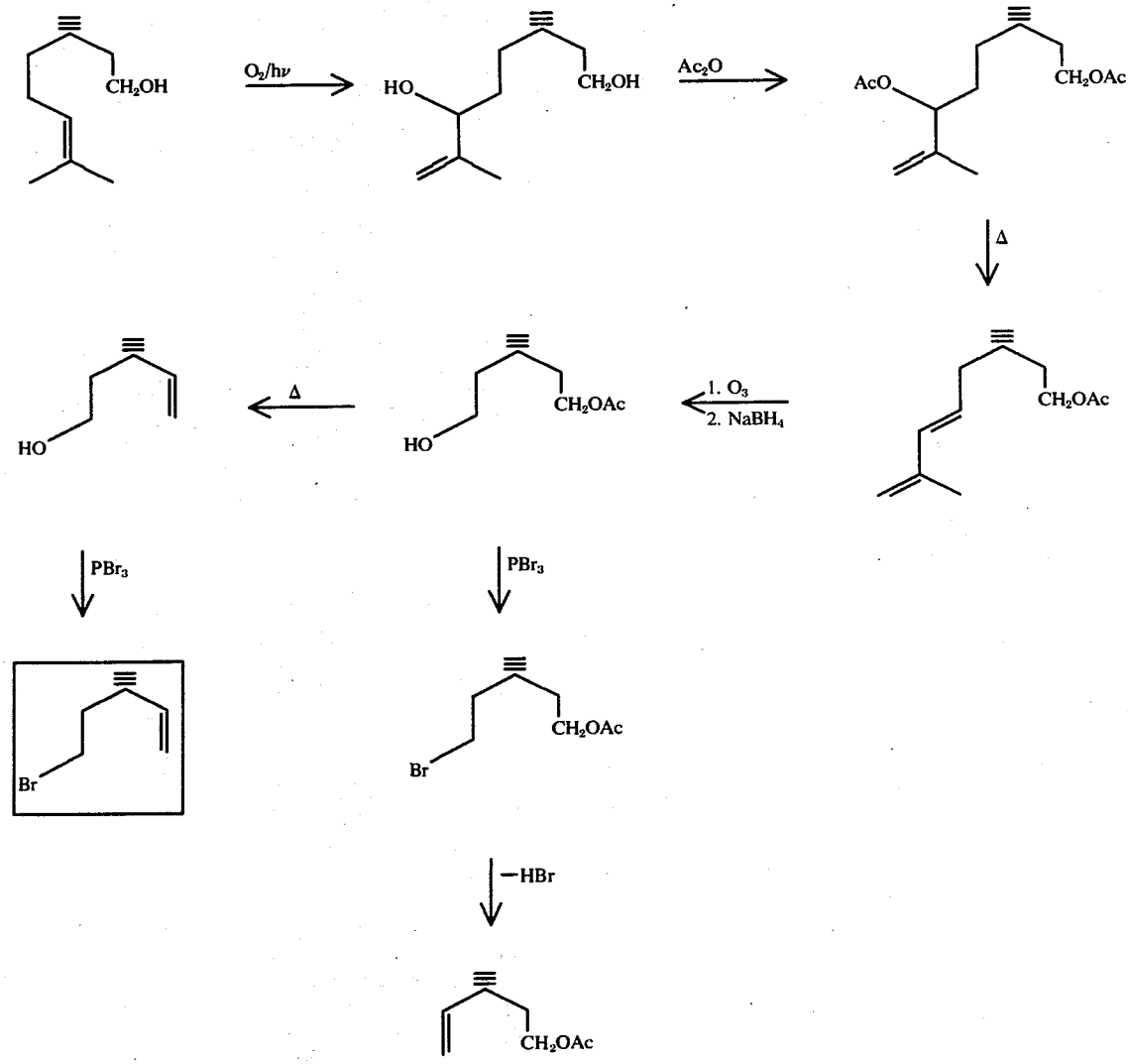

-continued

1. Saponification
2. PBr

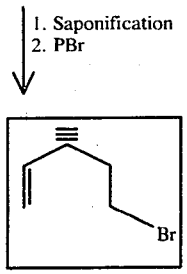

In the field of perfumery however, the racemic compounds obtained in accordance with the invention are perfectly suited for all practical purposes.

The invention is better illustrated by but not limited to the following Examples wherein the temperatures are indicated in degrees centigrade and the abbreviations have the meaning common in the art.

EXAMPLE 1

4,8,11,11-Tetramethyltricyclo[5.3.1.0$^{3,8}$]undec-9-en-7-ol

A. 0.500 g of a mixture containing equivalent amounts of the two diasteroisomers of 2,2,6-trimethyl-1-[3-methyl-pent-4-en-1-yl]-cyclohexa-3,5-dien-1-ol, obtained as indicated hereinbelow, and 0.025 g of potassium ter-butoxide in 8 ml of decaline were heated in an inert gas atmosphere in a sealed tube at 280° for 24 h. The reaction mixture was then diluted with diethyl ether, washed with water, dried over K$_2$CO$_3$ and finally concentrated. By bulb distillation 0.285 g of a fraction having B.p. 80°–100° /0.01 Torr were obtained. Pure 4,8,11,11-tetramethyltricyclo[5.3.1.0$^{3,8}$]undec-9-en-7-ol was isolated from the said fraction by vapour phase chromatography by means of a 5% silicon column, of 5 mm x 2.5 m, at 190° . The yield of the final product, calculated on the amount used of the diastereomeric mixture of the starting alcohols, was of about 30%.

B. By operating as indicated in paragraph A hereinabove and by using p-xylene as a solvent instead of decaline, the desired alcohol was obtained with a yield of about 24%. The spectral data of the obtained compound were the following:

NMR (CDCl$_3$, 90 MHz): 0.82 (3H, d, J = 6.5 cps); 0.91 (3H, s); 1.18 (6H, s); 5.81 (1H, d, J = 8 cps); 6.35 (1H, d of d, J$_1$ = 8 cps, J= 7 cps) δ ppm.

MS : M$^+$ = 220 (7); m/e: 205 (9), 202 (8), 187 (6), 177 (5), 159 (18), 145 (5), 132 (42), 119 (23), 107 (13), 93 (100), 86 (52), 71 (29), 55 (18), 43 (43), 41 (32).

2,2,6-trimethyl-1-[3-methyl-pent-4-en-1-yl]-cyclohexa-3,5-dien-1-ol, used as starting material in the above described process can be prepared as follows:

a. 3-Methyl-pent-4-en-1-ol

[see e.g.: Tetrahedron Letters, 1965, 4153; Bull. Soc. Chim. France, 1963, 1385].

A flow of ethylene oxide was bubbled through an etherial solution of but-2-en-1-yl-magnesium bromide until said oxide was absorbed in an amount of 9.5 g (0.21 M).

But-2-en-1-yl-magnesium bromide was previously prepared by a Grignard type reaction between 27 g (0.20 M) of but-2-en-1-yl bromide and 14.4 g (0.6 M) of magnesium powder in 200 ml of anhydrous ether.

The addition of ethylene oxide was strongly exothermic and the temperature of the reaction mixture was kept at about +10° by means of an external cooling. Once the addition was over, the reaction mixture was kept at room temperature under stirring overnight, then it was poured into a ice-water mixture and the whole was acidified with 2N HCl.

By extraction with ether, washing of the combined organic extracts with a saturated aqueous solution of sodium bicarbonate and water, drying over MgSO$_4$ and concentration 21 g of the desired raw material were obtained. This product consisted of a mixture of 3-methyl-pent-4-en-1-ol and hex-4-en-1-ol in a respective ratio of 3:1.

The desired product was isolated by a fractional distillation by using a Fischer type column (MS 300, 40 theoretical plates).

NMR (CCl$_4$, 60 MHz): 0.98 (3H, d, J = 6 cps); 1.47 (2H, d of t, J$_1$ = 6 cps, J$_2$ = 6 cps); 2.23 (1H, m); 3.52 (2H, t, J= 6 cps); 4.8 (1H, m); 5.03 (1H, m); 5.7 (1H, d of d of d, J$_1$ = 17 cps, J$_2$ = 9 cps, J$_3$ = 6.5 cps) δ ppm b. 3-Methyl-pent-4-en-1-yl bromide 1.6 ml (17 mM) of phosphorus tribromide were added under stirring and at a temperature of about 0°–3° to a mixture of 4.2 g (42 mM) of 3-methyl-pent-4-en-1-ol and 0.9 g of anhydrous pyridine. The addition took about 1 h, whereupon the reaction mixture was kept for 30 minutes at room temperature under vigourous stirring, then it was subjected to a distillation by using a Claisen type apparatus. There was thus obtained a fraction having B.p. 136°–9° which was then poured into a icewater mixture. This latter was extracted with pentane and the combined organic extracts were washed with a 10% aqueous NaOH solution and water, dried over MgSO$_4$ and concentrated to give 4.7 g (yield 68%) of the desired bromide.

NMR (CCl$_4$) 60 MHz: 1.0 (3H, d, J = 6 cps); 1.8 (2H, d of t, J$_1$ = 6 cps, J$_2$ = 6 cps); 2.31 (1H, m); 3.32 (2H, t, J = 6 cps); 4.85 (1H, m); 5.07 (1H, m); 5.65 (1H, d of d of d, J$_1$ = 16 cps, J$_2$ = 9 cps. J$_3$ = 6.5 cps) δ ppm c. 2,2,6-Trimethyl-1-1-/3-methyl-pent-4-en-1-yl/-cyclohexa-3.5-dien-1-ol 0.27 g (3mM) of lithium turnings containing 1.5% of sodium metal were added under an argon atomsphere at about −8° to a solution of 2.5 g (15mM) of 3-methyl-pent-4-en-1-yl bromide in 15 ml anhydrous ether. The thus obtained mixture was kept under stirring for 1 more hour at about 0°, whereupon it was filtered.

A solution of 1.02 g (7.5 mM) of 2,2,6-trimethyl-cyclohexa-3.5-dien-1-one [obtained according to the method described in Org. Synth, 46, 115 (1966)] was separated prepared by dissolving the said ketone at −60° in 7.5 ml of tetrahydrofuran. This cooled solution was then added dropwise at about 5°–10° to the lithium mixture prepared as indicated above. Once the addition was over, the reaction mixture was brought to room temperature and poured then in water and extracted with ether. The combined organic extracts were dried over $K_2CO_3$, concentrated to give a residue which upon distillation in a bulb apparatus gave 1.3 g of a fraction having B.p. 85°–105°/0.05 Torr. This fraction was constituted by a mixture (1:1) of the two diastereoisomers of the desired alcohol of formula

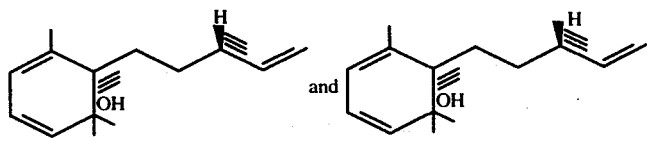

The purity of this mixture was of about 90% as indicated by an analysis by means of vapour phase chromatography using a 4% Supelco Sp-100, 3mm × 2.5 m column, at 140°–220°, 6°/min.

The spectral data of the obtained mixture were as follows:

NMR (CDCl$_3$, 60 MHz): 0.95(3H, d, J = 5.5 cps); 1.0 (6H, s); 1.81 (3H, s); 4.75 (1H, m); 4.98 (1H, m); 5.2-6.0 (4H) δ ppm MS : M$^+$ = 220 (19); m/e: 202 (9), 187 (1), 177 (1), 159 (1), 147 (19), 137 (100), 119 (44), 109 (27), 91 (18), 77 (12), 69 (9), 55 (25), 43 (22), 41 (22).

EXAMPLE 2

4,8,11,11-Tetramethyltricyclo[5.3.1.0$^{3,8}$]undecan-7-ol 4,8,11,11-Tetramethyltricyclo[5.3.1.0$^{3,8}$]undec-9-en-7-ol, prepared according to the process described in Example 1, was catalytically hydrogenated in the presence of PtO$_2$, in accordance with the process described by G. Büchi et al, J. Am. Chem. Soc., 83, 927 (1961). The product obtained was in all respects identical to that prepared by the cited authors.

EXAMPLE 3

The preparation of 4,8,11,11-tetramethyltricyclo [5.3.1.0$^{3,8}$]-undec-9-en-7-ol in the form of one of its enantiomers was carried out starting from optically active starting materials. Thus, the preparation of one of the enantiomers of 3-methyl-pent-4-en-1-yl bromide of formula

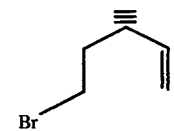

was carried out as follows:
a. reaction scheme:

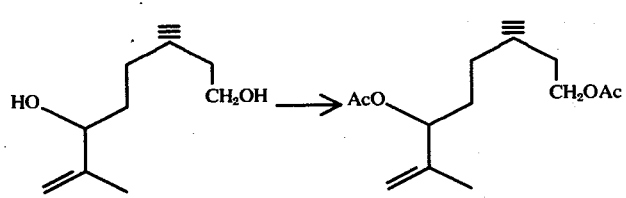

408 g (4M) of acetic anhydride were added under stirring to a solution of 3,7-dimethyl-6-hydroxy-oct-7-en-1-ol (344 g, 2 M, Firmenich SA, Geneva) in 400 ml of pyridine. The reaction mixture was kept under stirring for 3 h, whereupon it was extracted with ether and the combined organic extracts were washed until neutrality with an aqueous NaOH solution. 441 g (yield 86.4%) of the desired diacetate were obtained. An analytical sample has shown the following characteristics:

IR : 1740 and 890 cm$^{-1}$
MS : m/e: 136 (6), 121 (29), 55 (17), 43 (100).
NMR: 0.95 (3H, d, J = 6 cps); 1.70 (3h, s); 1.97 (3H, s); 2.00 (3H, s); 4.03 (2H, t, J = 6 cps); 4.87 (2H, broad band)
5.07 (1H, t, J = 6 cps) δ ppm [α]$_D^{20}$ −4° b. reaction scheme

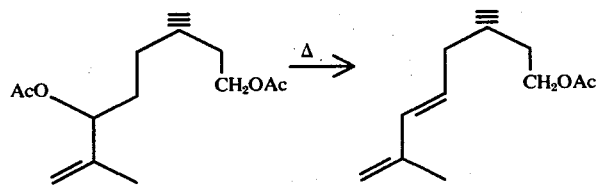

440 g of the diacetate prepared according to the hereinabove indicated process were subjected to a pyrolysis at 430°/15 Torr in a quartz tube of 1 m. length. By distilling the pyrolisate, 164 g of the desired product were isolated at B.p. 62°/01 Torr; [α]$_D^{20}$ −8.1°
IR : 1740, and 890 cm$^{-1}$ NMR: 0.95 (3H, d, J = 6 cps); 1.83 (3H, s); 2.00 (3H, s); 4.05 (2H, t, J = 6 cps); 4.82 (2H, s); 5.3-6.3 (2H, m) δ ppm c. reaction scheme

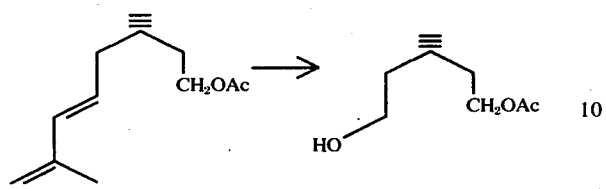

160 g of the acetate obtained according to paragraph (b) above were dissolved in 200 ml of methanol and subjected to ozonisation at about −15° by using a ozone flow of about 5g/h during 7 h.

The solution obtained was then treated with a mixture of 150 g of NaBH$_4$ in 300 ml of ethanol at a temperature of from about −10° to + 10°, whereupon the mixture was kept under stirring at this temperature during ½h. The reaction mixture was poored into an excess of water and extracted then with ether. The combined organic extracts after the usual working up gave a residue which on fractional distillation yielded 94 g of a mixture having B.p. 50°–75°/0.1 Torr. A further purification of this mixture by means of column chromatography gave 35 g of the desired hydroxyacetate.

$[\alpha]_D^{20}$ +3.1° d. reaction scheme

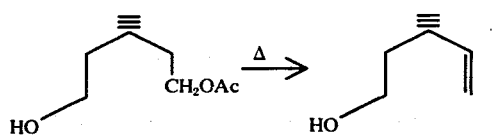

20 g of the hydroxyacetate obtained as indicated sub letter (c) above, were subjected to a pyrolysis in a filled quartz tube of 40 cm length. The pyrolysate collected was washed with an aqueous solution of sodium bicarbonate and fractionally distilled to give 6.2 g of a fraction having B.p. 60°/20 Torr (yield 49.5 %). $[\alpha]_D^{20}$ +11°

IR : 3350 and 910 cm$^{-1}$

NMR: 1.05 (3H, d, J = 7 cps); 1.52 (2H, q, J = 7 cps); 2.35 (1H, quint., J = 7 cps); 3.1 (1H, s); 3,56 (2H, t, J = 7 cps); 4.77–5.95 (3H, m) δ ppm e. reaction scheme

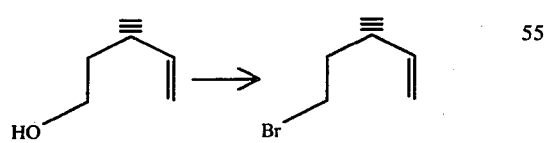

2 ml of phosphorus tribromide in 30 ml of petrol ether were added dropwise under stirring to a solution of 6.2 g of the alcohol prepared in accordance with letter (d) above in 30 ml of petrol ether.

The reaction mixture was then left at room temperature overnight, whereupon it was poured into ice. After the washing of the separated organic phases with an aqueous sodium bicarbonate solution and water until neutrality, the organic phases gave on evaporation and fractional distillation a product having B.p. 39°/19 Torr; $[\alpha]_D^{20}$ + 21.9°

IR : 910 cm$^{-1}$

NMR: 1.07 (3H, d, J = 7 cps); 1.83 (2H, q, J = 7cps); 2.42 (1H,) (quint., J = 7 cps); 3.35 (2H, t, J = 7 cps); 4.8-5.95 (3H, m) δppm

EXAMPLE 4

Perfume composition

A base perfume composition for after-shave was obtained by mixing together the following ingredient (parts by weight):

| | |
|---|---|
| Absolute oak-moss | 20 |
| Benzyl salicylate | 20 |
| Coumarin | 20 |
| Isoeugenol | 20 |
| Musk ambrette | 30 |
| Musk ketone | 30 |
| Pentadecanolide at 10 %* | 20 |
| Synth. absolute Jasmin at 50 %* | 100 |
| Artificial bulgarian Rose oil | 20 |
| Citronellol | 50 |
| Lavender oil | 100 |
| Olibanum | 20 |
| Citronellyl acetate | 40 |
| Hydroxycitronellal | 50 |
| Vetiver Bourbon | 20 |
| Marjoram | 30 |
| Terpeneless Juniper oil | 20 |
| Limet | 60 |
| Sweet orange oil at 50 %* | 100 |
| Artificial Neroli | 40 |
| Galbanum | 5 |
| Artificial Bergamot | 100 |
| Oriental sandel wood | 20 |
| α-Isomethyl-ionone | 65 |
| Total | 1000 |

*in diethyl phthalate

By using the above indicated base perfume composition, two novel compositions, A and B, were obtained by mixing A : 95 g of the base composition with 5 g of patchouli oil, and B: 96 g of the base composition with 4 g of 4,8,11,11-tetramethyltricyclo[5.3.1.0$^{3,8}$]-undec-9-en-7-ol.

The two novel compositions were subjected to the evaluation of a group of experienced perfumers who had to express their view on their olfactive properties.

It was found that the two compositions had analogous odoriferous effects, both possessed a rich, tenacious and smooth earthy character.

What is claimed is:

1. A process for the preparation of a compound of formula (I)

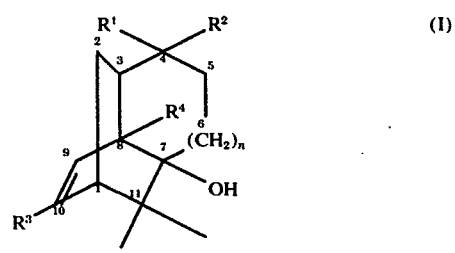

and wherein:
each of symbols R$^1$, R$^2$, R$^3$ and R$^4$, identical or different, represents a hydrogen atom or an alkyl radical containing from 1 to 6 carbon atoms, and the index n stands for zero or 1 which comprises reacting

A hydroxyl compound of formula (II)

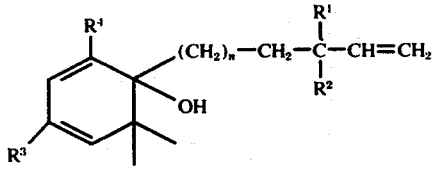

wherein the index n and the symbols $R^1$, $R^2$, $R^3$ and $R^4$ have the aforementioned meaning, at a temperature from about 200° to about 400° C and a pressure of from about 1 to 20 atmospheres, with a strongly basic agent, to yield the compound of formula (I).

2. A process according to claim 1, wherein the reaction is carried out at a pressure above 20 atmospheres and at a temperature below 200° C.

3. A process according to claim 1 for the preparation of a compound of formula III

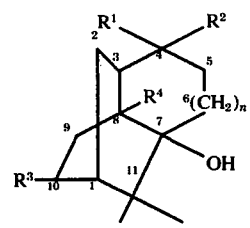

wherein a compound of formula I is catalytically hydrogenated to obtain an unsaturated product.

4. A process according to claim 1, wherein the strongly basic agent is a strong mineral or an organic base selected from the group consisting of alkali metal hydroxides or alkoxides.

5. A process according to claim 4, wherein the alkali metal alkoxide has a sterically hindered reactive center.

6. A process according to claim 5, wherein the alkali metal alkoxide is sodium or potassium ter-butylate.

7. A process according to claim 6, wherein sodium or potassium ter-butylate is present in the reaction medium at a concentration of between about 1 and 10% by weight based on the weight of the starting hydroxyl compound of formula (II).

8. A process according to claim 1, wherein the temperature is of about 230° to 320° C.

9. A process according to claim 1, wherein the compound of formula (II) is 2,2,6-trimethyl-1-[3-methyl-pent-4-en-1-yl]-cyclohexa-3,5-dien-1-ol and the obtained compound of formula (I) is 4,8,11,11-tetramethyltricyclo[5.3.1.0$^{3,8}$]undecan-7-ol.

* * * * *

UNITED STATES PATENT AND TRADEMARK OFFICE
CERTIFICATE OF CORRECTION

PATENT NO. : 4,011,269

DATED : March 8, 1977

INVENTOR(S) : Ferdinand Näf, Gunther Ohloff

It is certified that error appears in the above-identified patent and that said Letters Patent are hereby corrected as shown below:

Column 2, line 38, "Through" should read --Though--.

Column 2, line 39, "construced" should read --construed--.

Column 3, line 24, "support support" should read --support--.

Column 4, line 25, "3.8" should read --3,8--.

Column 4, line 50, "Sec." should read --Soc.--.

Column 5, line 1, "5.3.1.0 $^{3.8}$]" should read -- [5.3.1.0 $^{3,8}$] --.

Column 5, line 3, "[5.3.1.0 $^{3.8}$]" should read -- [5.3.1.0 $^{3,8}$] --.

Columns 7 and 8, center of page, "2. PBr" should read --2. $PBr_3$--.

Column 7, line 51, "J=7 cps)" should read --$J_2$= 7 cps)--.

Column 8, line 58, "=9 cps." should read -- =9 cps, --.

Column 9, line 4, "separated prepared" should read --separately prepared--.

UNITED STATES PATENT AND TRADEMARK OFFICE
CERTIFICATE OF CORRECTION

PATENT NO. : 4,011,269
DATED : March 8, 1977
INVENTOR(S) : Ferdinand Näf, Gunther Ohloff It is certified that error appears in the above-identified patent and that said Letters Patent are hereby corrected as shown below:

Column 10, line 67, "B.p. 62°/01 Torr" should read -- B.p. 62°/0.1 Torr --.

Column 11, line 31, "+3.1°" should read -- +2.1° --.

Column 12, line 6, "(1H,) (quint.," should read --(1H,quint.,--.

Column 12, line 44, "-undec-9" should read -- undec-9 --.

Signed and Sealed this

Fourth Day of April 1978

[SEAL]

Attest:

RUTH C. MASON
Attesting Officer

LUTRELLE F. PARKER
Acting Commissioner of Patents and Trademarks